(12) United States Patent
Leistner et al.

(10) Patent No.: US 8,702,663 B2
(45) Date of Patent: Apr. 22, 2014

(54) EYEWASH CONTAINER

(75) Inventors: Steven C. Leistner, Beamsville (CA); Ronya Ripenburg, Catharines (CA); Michael D. Murphy, Evergreen Park, IL (US)

(73) Assignee: Niagara Pharmaceuticals Inc., Flamborough (CA)

( * ) Notice: Subject to any disclaimer, the term of this patent is extended or adjusted under 35 U.S.C. 154(b) by 29 days.

(21) Appl. No.: 13/274,810

(22) Filed: Oct. 17, 2011

(65) Prior Publication Data

US 2013/0096517 A1 Apr. 18, 2013

(51) Int. Cl.
*A61H 33/04* (2006.01)
*A61M 35/00* (2006.01)

(52) U.S. Cl.
USPC .......................................... 604/301; 604/295

(58) Field of Classification Search
USPC .......................... 604/294–302; 215/218–221; 222/420–421
See application file for complete search history.

(56) References Cited

U.S. PATENT DOCUMENTS

| | | | |
|---|---|---|---|
| 3,872,866 A | 3/1975 | Lelicoff | |
| 3,917,119 A * | 11/1975 | Kahn | 222/108 |
| 5,449,098 A * | 9/1995 | Offman | 222/481.5 |
| 6,488,165 B1 * | 12/2002 | Hidding | 215/344 |
| 6,540,726 B1 * | 4/2003 | Follman et al. | 604/294 |
| 6,981,600 B1 | 1/2006 | Battezazzore | |
| 7,621,897 B1 * | 11/2009 | Berke | 604/295 |
| 8,444,610 B2 * | 5/2013 | Grevin | 604/298 |
| 2007/0204398 A1 | 9/2007 | Dubois | |
| 2008/0281280 A1 * | 11/2008 | Jaworski et al. | 604/301 |
| 2009/0043269 A1 * | 2/2009 | Skou et al. | 604/298 |

FOREIGN PATENT DOCUMENTS

| | | |
|---|---|---|
| EP | 2347749 A1 | 1/2010 |
| JP | 2000-262584 A | 9/2000 |
| JP | 2005-021254 A | 1/2005 |
| WO | 87/02237 A1 | 4/1987 |

OTHER PUBLICATIONS

Print-out from www.usplastic.com of Plum Eye Wash Station (printed Sep. 29, 2011).
Print-out from www.plumbalert.com (printed Sep. 29, 2011).
Print-out from www.bealert.com (printed Sep. 29, 2011).
International Search Report and Written Opinion from PCT Application No. PCT/US2012/060628 entitled Eyewash Container (Dated Mar. 29, 2013).

* cited by examiner

*Primary Examiner* — Jackie Ho
*Assistant Examiner* — Mark K Han
(74) *Attorney, Agent, or Firm* — Hovey Williams LLP

(57) ABSTRACT

An eyewash dispensing container to store and deliver an eyewash fluid that is particularly suitable for terminal sterilization. The container includes a base and a locking lid with a tamper indicator. The container is able to be opened quickly and deliver the eyewash fluid directly to an eye of a user.

16 Claims, 9 Drawing Sheets

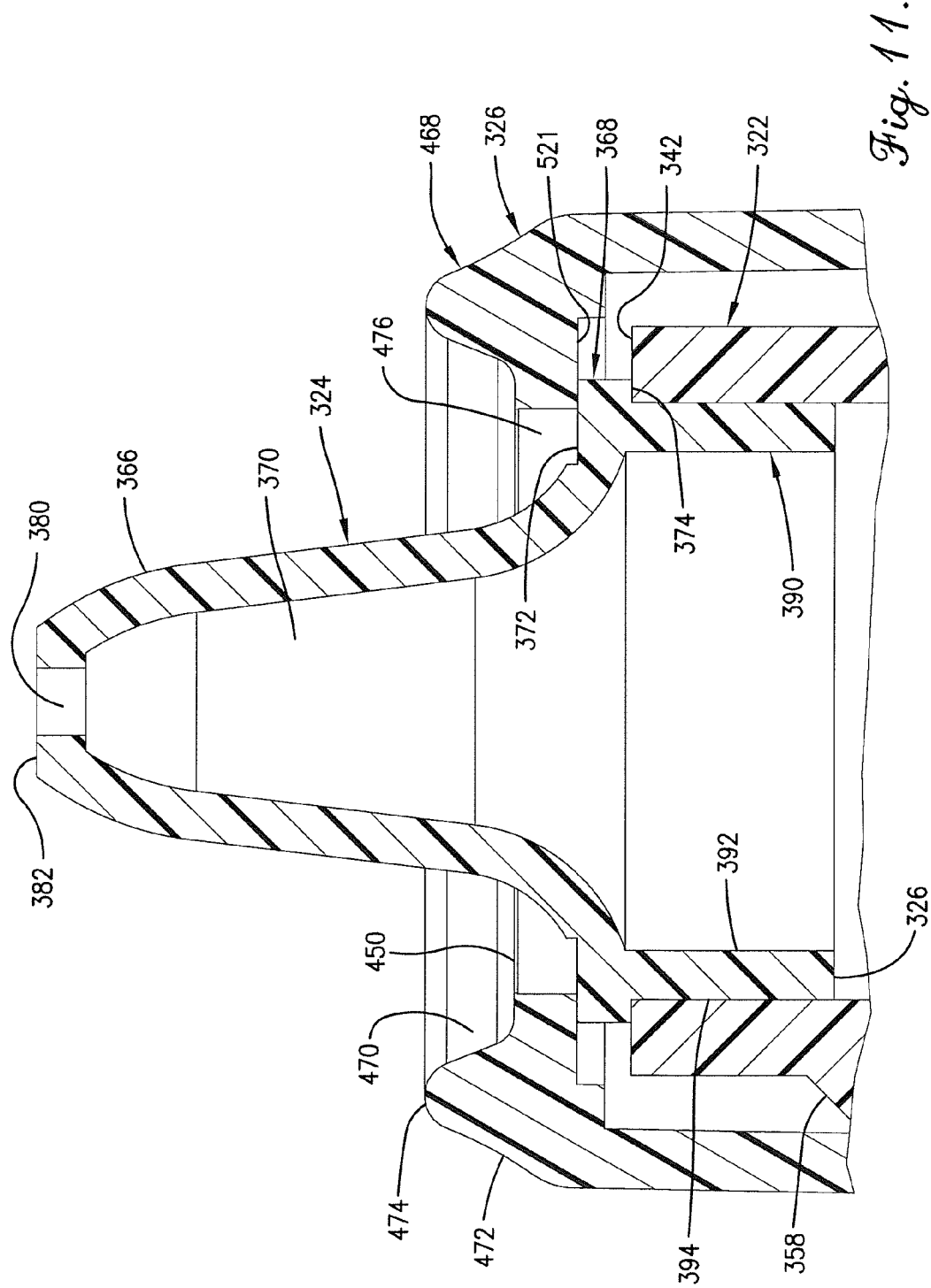

EYEWASH CONTAINER

BACKGROUND

1. Field of the Invention

The present invention relates generally to eyewash storage and delivery containers. More specifically, embodiments of the present invention concern a storage and delivery container operable to be filled with an eyewash fluid, fitted with a locking lid, and terminally sterilized.

2. Description of the Related Art

Containers to store fluids are widely used for various applications in which it is desirable to ensure that stored fluids are sterilized and remain sterilized during storage. It is also desirable to know whether tampering has occurred with respect to containers storing fluid. Generally, tamper indicators are not designed to prevent tampering, but to indicate whether tampering has occurred.

Fluids and conventional containers to store such fluids are commonly sterilized separately and brought together during a filling operation in a sterile environment. However, such manufacturing operations do not necessarily ensure sterility of the fluid and container until use.

It is also known to sterilize containers using a terminal sterilization process, which involves sterilization after container has been filled with the fluid; that is, with the packaged product in its final, assembled form. Terminal sterilization is commonly performed by irradiating or steam treating the packaged product. For complete terminal sterilization, however, containers must be manufactured of a material that permits the terminal sterilization process (e.g., allows gamma rays to pass therethrough) without losing its structural integrity.

Moreover, many conventional containers are not equipped with tamper indicators on components such as the eyecup, which is undesirable for a variety of applications. For instance, in emergency treatment applications where it is desirable to cleanse or rinse one or both eyes of the user, it is generally desirable to ensure that not only the eyewash fluids and containers have been sterilized, but the fluid dispensing component (e.g., eyecup) is sterilized and has not been subjected to any tampering. Thus, many conventional containers are deficient in this regard.

Additionally, many conventional emergency eyewash treatment devices utilize a separate dispensing cup to aid in delivery of eyewash fluids from the storage container to one or both eyes of the user. Such separate dispensing cups are problematic because they present another element for which it is desirable to sterilize and maintain sterility. Additionally, it may be necessary to fill the conventional cups several times before satisfactorily performing the emergency eyewash treatment. In conducting emergency eyewash treatments, time is of the essence. The additional time required to both fill and refill the conventional cups is problematic because any additional time consumed may aggravate any injuries to the eyes of the user. Furthermore, if the user is the person requiring the eyewash treatment, the user's vision is likely impaired, which causes manipulation of the cup to be difficult and often problematic.

SUMMARY

The following summary is provided to indicate the nature of the subject matter disclosed herein. While certain aspects of the present invention are described below, the summary is not intended to limit the scope of the present invention.

Embodiments of the present invention provide an eyewash storage and delivery system that does not suffer from the aforementioned problems and limitations of conventional containers, such as those set forth above. Additionally, the present invention is easily and economically manufactured and easily used.

According to certain aspects of the present invention, an eyewash dispensing container includes a closure that sealingly overlies the dispensing component (e.g., eyecup) and is provided with a tamper indicator. The container is assembled to store an eyewash fluid that may be terminally sterilized after the container has been sealed with the eyewash fluid contained therein. Consequently, the eyewash storage and dispensing system is able to be opened quickly and deliver the eyewash fluid directly to an eye of a user, while ensuring the sterilized condition of the contents and dispensing component use.

The aforementioned aspects may be achieved in one aspect of the present invention by providing an eyewash dispensing container. The container may include a base presenting a storage cavity in which eyewash fluid is contained. The base may include a neck that defines an opening in communication with the cavity to permit fluid to be discharged from the base. The container may further include a fluid dispensing cap sealingly secured to the base in a covering relationship with the opening. The dispensing cap may include a fluid outlet through which fluid is discharged from the storage cavity. The dispensing cap may include a cap skirt circumscribing the neck of the base. The cap skirt and neck may cooperatively present interlocking structure to restrict removal of the dispensing cap from the base. The container may further include a removable closure sealingly overlying the dispensing cap to prevent fluid dispensing until removed. The closure may provide tamper indication once removed so as to facilitate only single use of the container.

The aforementioned aspects may be achieved in another aspect of the present invention by providing a method of filling an eyewash dispensing container. The method may include the steps of (a) at least partially filling a container base with eyewash fluid and (b) sealingly securing a fluid dispensing cap of the container to the base in a covering relationship with a base opening. The step (b) may include the step of interlocking the dispensing cap and base so as to prevent removal of the cap from the base. The method may further include the step of (c) sealingly covering the dispensing cap with a removable container cover that prevents fluid dispensing until removed, wherein the cover provides tamper indication once removed so as to facilitate only single use of the container. After steps (a)-(c) have been completed, the method may include the step of sterilizing the container and the fluid.

Other aspects and advantages of the present invention will be apparent from the following detailed description of the preferred embodiments and the accompanying drawings figures.

BRIEF DESCRIPTION OF THE FIGURES

Embodiments of the present invention are described herein with reference to the following drawing figures, wherein:

FIG. 6 is a partial exploded perspective view of the eyewash dispensing container illustrated in FIG. 1, illustrating the cup secured to the container and the closure exploded from the cup;

FIG. 11 is an enlarged, fragmentary cross-sectional view of the eyewash dispensing container illustrated in FIG. 8.

Figure 1:
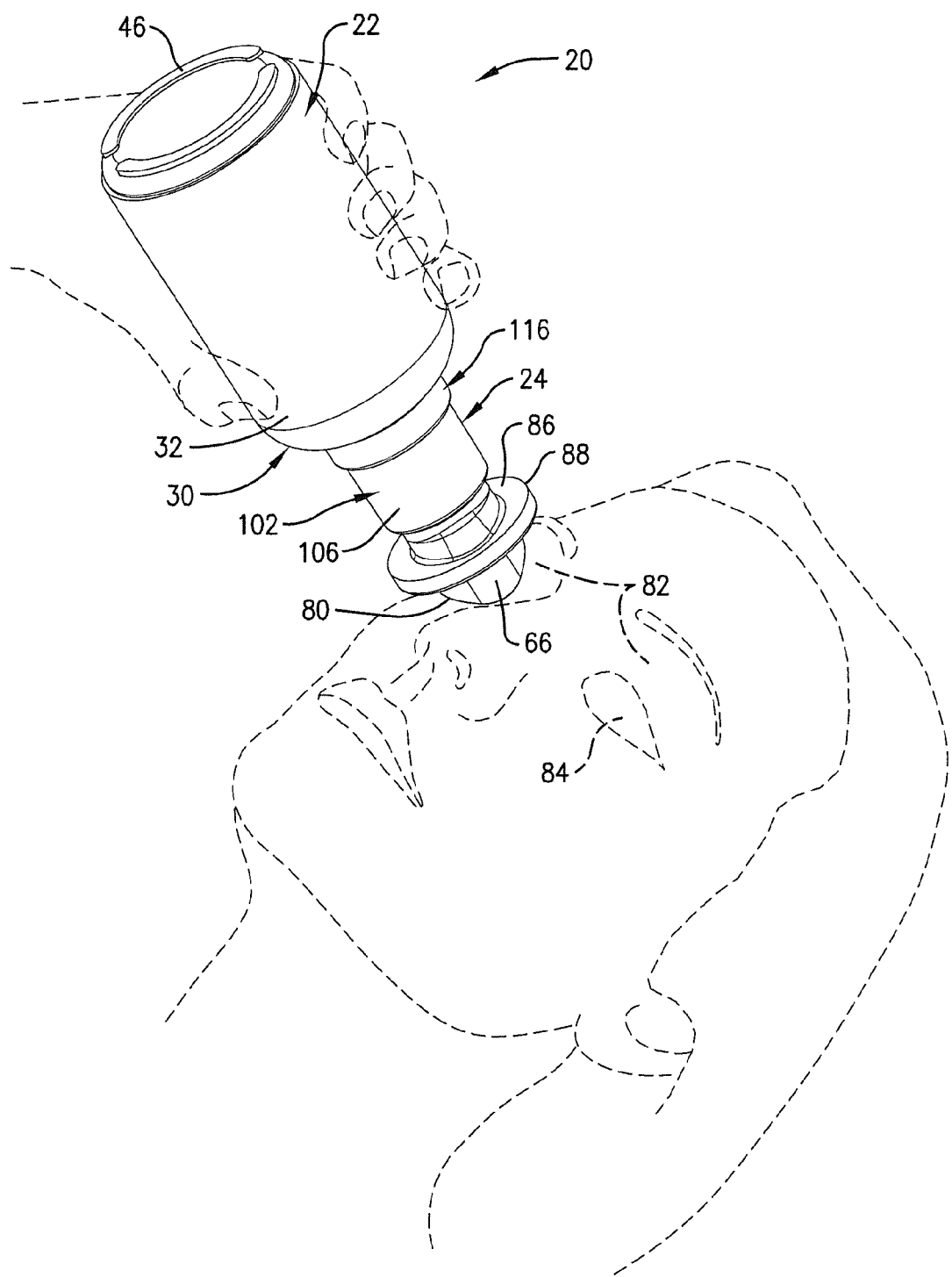
FIG. 1 is a perspective view of an eyewash dispensing container in accordance with an exemplary embodiment of the present invention illustrating the system in use with a user.

The drawings do not limit the present invention to the specific embodiments disclosed herein. The drawings are not necessarily to scale, emphasis instead being placed upon clearly illustrating the principles of the preferred embodiment.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning to the drawings and particularly FIGS. 1-4, a fluid storage and delivery system is generally illustrated in accordance with an exemplary embodiment of the present invention. The system generally includes an eyewash dispensing container 20 having a base 22, a fluid-dispensing cap 24, and a removable container cover or closure 26, which are assembled together to store an eyewash fluid 28, such as a saline solution or the like. Particularly, the cap 24 is securely engaged with and fitted to the base 22 and the closure 26 is securely engaged with and fitted to the cap 24. The base 22, the cap 24, and the closure 26 are of a similar shape and material, such as but not limited to a plastic resin or the like, to ensure secure engagement therebetween.

The base 22 includes a body 30 with opposing outer and inner surfaces 32, 34. The outer surface 32 of the base 22 presents a grasping surface for the user to handle the system 20. The inner surface 34 of the base 22 defines a storage cavity 36 within the base 22 operable to store the fluid 28. In the exemplary embodiment, the base 22 is of a generally cylindrical shape. It is foreseen, however, that the base 22 may be of any shape without deviating from the scope of the present invention.

Figure 2:
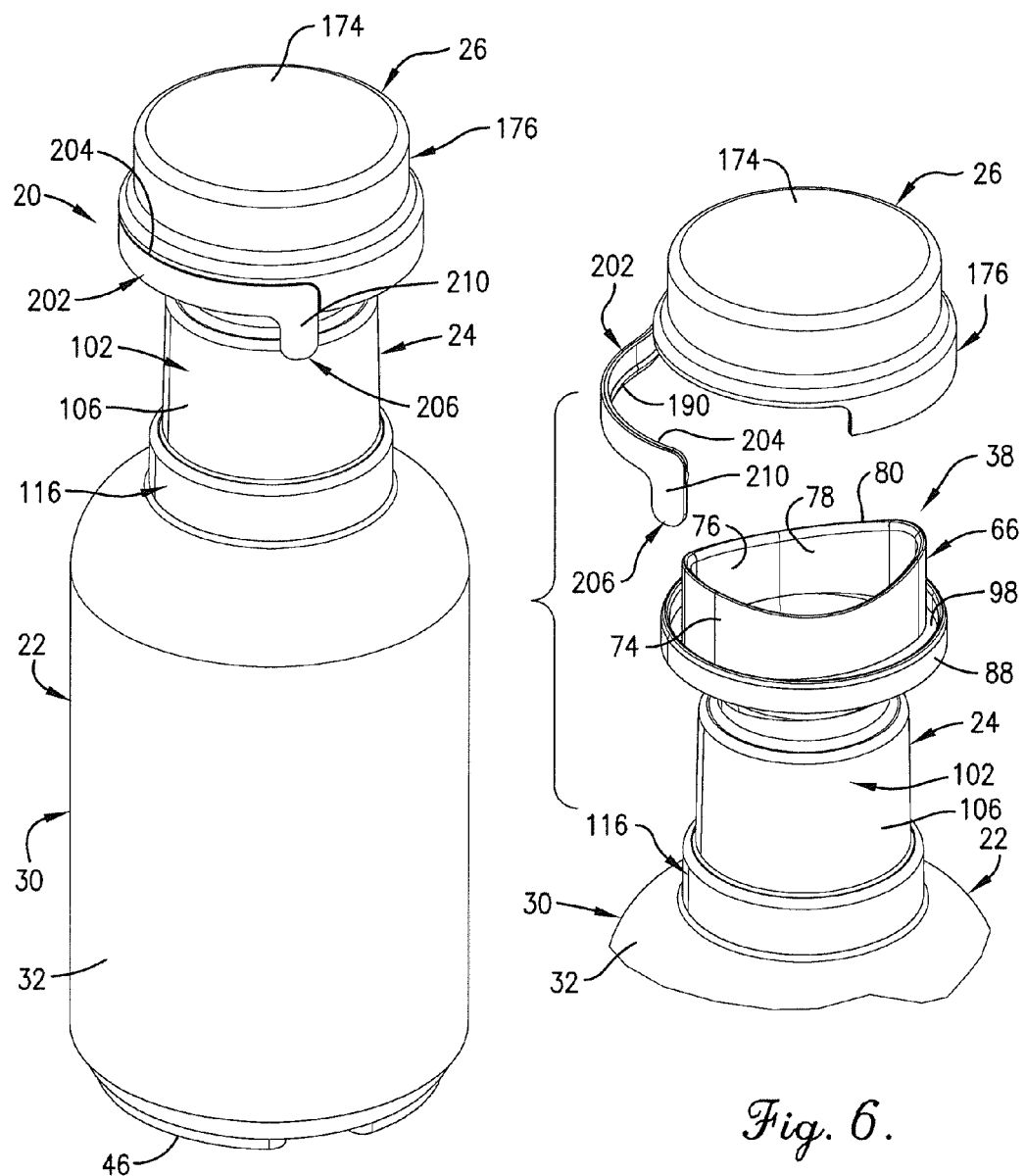
FIG. 2 is a perspective view of the eyewash dispensing container illustrated in FIG. 1, illustrating a cup secured to a container and a closure secured to the cup.
Figure 3:
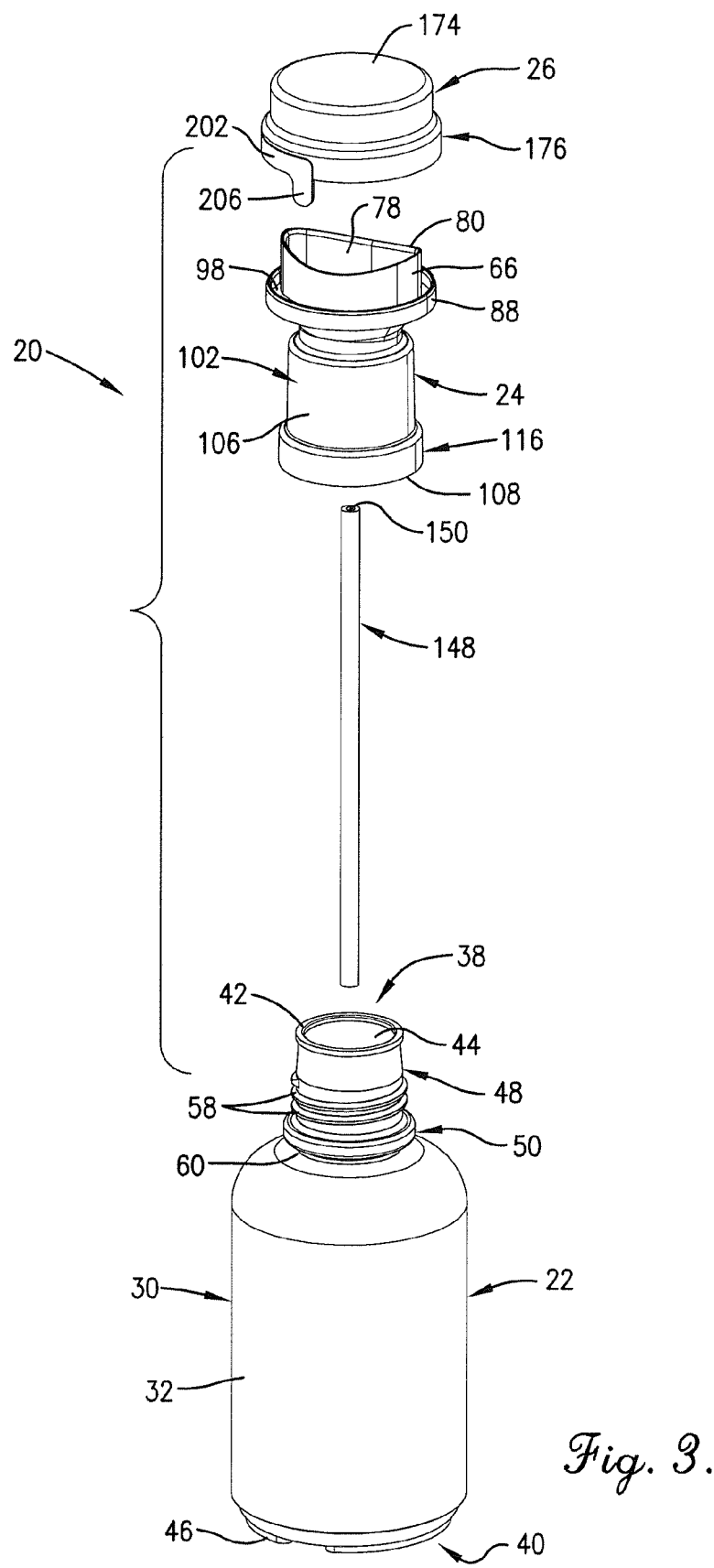
FIG. 3 is an exploded perspective view of the eyewash dispensing container illustrated in FIG. 1, illustrating the closure exploded from the cup, the cup exploded from the container, and a closure exploded from the cup.
Figure 4:
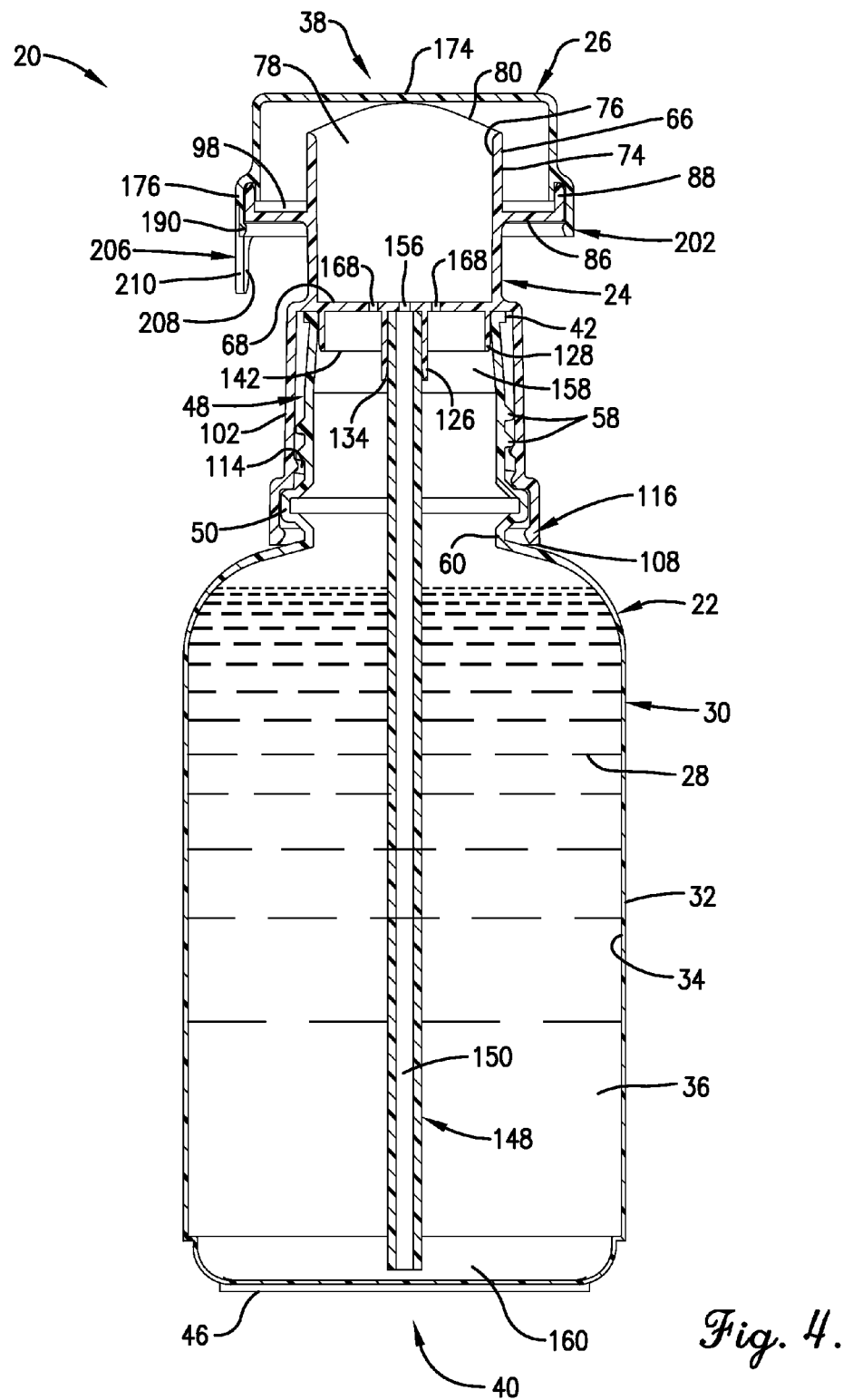
FIG. 4 is a cross-sectional view of the eyewash dispensing container illustrated in FIG. 1.

The storage cavity 36 is open at an open end 38 of the base 22 and closed at a closed end 40 of the base 22. The open end 38 includes a circumferential lip 42 that defines an opening or mouth 44 through which the fluid 28 is received in and/or dispensed from the storage cavity 36. The closed end 40 of the base 22 includes an end wall 46 operable to support the container 20 in an upright configuration, as illustrated by FIG. 2.

Figure 5:
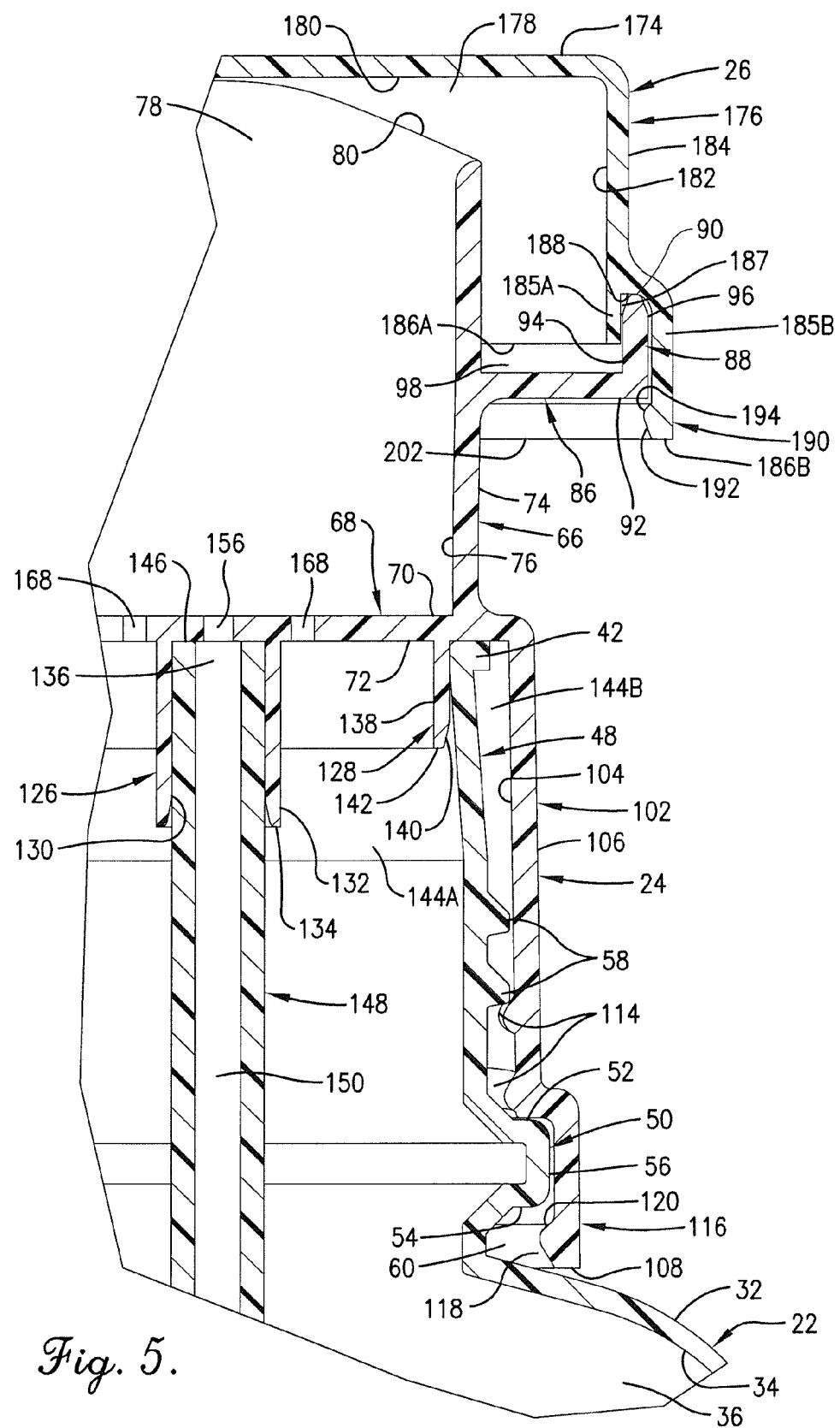
FIG. 5 is a magnified, fragmentary, cross-sectional view of the eyewash dispensing container illustrated in FIG. 1.

The base 22 tapers when traveling from the closed end 40 to the open end 38 and ultimately presents a neck 48. The neck 48 includes a circumferential rib 50 that protrudes axially or outwardly from the base 22 and is defined by opposing upper and lower horizontal surfaces 52, 54 that are spaced from each other by a vertical surface 56, which is a portion of the outer surface 32 of the base 22, as illustrated in FIG. 5. Also protruding outwardly from the neck 48 of the base 22 is an external thread 58, which is oriented between the rib 50 and the open end 38 along the neck 48 of the base 22. On a side of the rib 50 opposite to the thread 58 is a receiver portion 60 of the neck 48. The receiver portion 60 has a smaller circumference than a circumference of the rib 50.

The cap 24 is sized and shaped to securely mate with the neck 48 of the base 22 and is, in the exemplary embodiment, of a generally cylindrical shape. It is foreseen, however, that the cap 24 may be of any shape without deviating from the scope of the present invention. The cap 24 includes a circumferential perimeter wall or splashguard 66 that extends upwardly from a medial wall or divider 68. The divider 68 has opposing upper and lower surfaces 70, 72. The splashguard 66 extends upwardly from the upper surface 70 of the divider 68.

The splashguard 66 includes opposing outer and inner surfaces 74, 76 that cooperatively define a fluid-dispensing area 78 within the cap 24. On an opposite end of the splashguard 66 relative to the divider 68 is an ocular-engagement edge 80 shaped to engage and generally conform to a facial contour 82 around an eye 84 of the user. The fluid 28 is thereby directed to the eye 84 of the user and substantially contained within a vicinity thereof via the splashguard 66. In the exemplary embodiment, the ocular-engagement edge 80 and the splashguard 66 have an oval shape, similar to that of the eye 84 of the user. It is foreseen, however, that the splashguard 66 and the ocular-engagement edge 80 may have any shape without deviating from the scope of the present invention.

Spaced radially from the outer surface 74 of the splashguard 66 by a spacer wall 86 is a perimeter sidewall 88 that extends substantially parallel to the splashguard 66. The sidewall 88 includes opposing upper and lower edges 90, 92 that are spaced from each other by opposing interior and exterior surfaces 94, 96. The spacer wall 86 and the perimeter sidewall 88 cooperatively define a circumferential channel 98 that extends around the splashguard 66. The channel 98 is operable to catch and contain any of the fluid 28 that is inadvertently spilled out of the cap 24. While it is foreseen that the perimeter wall 88 may have any shape, in the exemplary embodiment, the perimeter wall 88 is of a substantially circular shape. Thus, due to the oval shape of the splashguard 66, the spacer wall 86 extends from the outer surface 74 of the splashguard 66 at variable lengths around the splashguard 66, which causes the channel 98 to have a variable width around the splashguard 66.

The cap 24 further includes a base-engagement skirt 102 that depends from the lower surface 72 of the divider 68. The base-engagement skirt 102 has opposing inner and outer surfaces 104, 106. On an opposite end of the base-engagement skirt 102 relative to the divider 68 is a container-abutment edge 108, as illustrated in FIG. 5. Protruding inwardly from the inner surface 104 of the base-engagement skirt 102 is an internal thread 114, which is sized and shaped to securely mate with the external thread 58 of the neck 48 of the base 22. In this manner, a secure engagement between the cap 24 and the base 22 is formed when the cap 24 is threaded onto the neck 48 of the base 22.

Also protruding axially or inwardly from the inner surface 104 of the base-engagement skirt 102 and between the internal thread 114 and the container-abutment edge 108 is a first locking element 116. The first locking element 116 is defined by first and second surfaces 118, 120 that are oblique relative to the axial direction of extension of the first locking element 116. The first surface 118 extends from the container-abutment edge 108 to the second surface 120 and is angled at approximately 30° from a plane defined by the inner surface 104 of the base-engagement skirt 102. The second surface 120 extends from the first surface 118 to the inner surface 104 of the base-engagement skirt 102 and is angled at approximately 45° from the plane defined by the inner surface 104 of the base-engagement skirt 102.

When the cap 24 is fitted to the base 22, the first surface 118 of the first locking element 116 abuts the upper horizontal surface 52 of the rib 50. Due to the lesser angle of the first surface 118, that is, approximately 30°, the first locking element 116 slides over the rib 50 and is received by the receiver portion 60 of the neck 48. When removal of the cap 24 from the base 22 is attempted, the second surface 120 of the first locking element 116 abuts the lower horizontal surface 54 of the rib 50. Due to the greater angle of the second surface 120, that is, approximately 45°, the first locking element 116 is prevented from sliding over the rib 50. In this manner, the first locking element 116 securely locks the cap 24 to the base 22 after being fitted thereto.

The cap 24 further includes circumferential inner and outer conduits 126, 128 depending from the lower surface 72 and within the base-engagement skirt 102 of the divider 68. The inner conduit 126 has opposing inner and outer surfaces 130, 132 spaced from each other by an inner conduit lip 134. The inner conduit 126 defines an inner conduit passageway and receiver 136. The outer conduit 128 has opposing inner and outer surfaces 138, 140 spaced from each other by an outer conduit lip 142. The inner and outer surfaces 138, 140 of the outer conduit 128 cooperatively define an outer conduit passageway 144A and an outer conduit receiver 144B on either side of the outer conduit 128.

The inner conduit passageway and receiver 136 is sized and shaped to securely receive a first end 146 of a tube 148 having an elongated passageway 150 that terminates at a second end 152 of the tube 148. The first end 146 of the tube 148 is secured in the inner conduit passageway and receiver 136 via friction fit in the exemplary embodiment to provide a seal therebetween, but it is foreseen that an adhesive or the like may be used in addition to or in lieu of the friction fit engagement. The tube 148 is sized and shaped to extend from the mouth 44 of the base 22 and substantially through the storage cavity 36 of the base 22. Thus, when the tube 148 is affixed to the inner conduit 126 of the cap 24 and the cap 24 is fitted to the base 22, the first end 146 of the tube 148 is adjacent to the open end 38 of the base 22 and the second end 152 of the tube 148 is adjacent to the closed end 40 of the base 22.

A vent hole 156 extends between the surfaces 70, 72 of the divider 68 and provides communication to and/or from the inner conduit passageway and receiver 136 and the fluid dispensing area 78 of the cap 24. The tube 148 provides communication to and/or from the inner conduit passageway and receiver 136 at an upper first portion 158 of the storage cavity 36 and a lower second portion 160 of the storage cavity 36. While the exemplary embodiment is illustrated with the single vent hole 156 in the cap 24, it is foreseen that the cap 24 may be equipped with any number of vent holes, such as but not limited to two vent holes, without deviating from the scope of the present invention.

The outer conduit receiver 144B is sized and shaped to securely receive the neck 48 of the base 22 so that the lip 42 simultaneously abuts the lower surface 72 of the divider 68 and the outer surface 140 of the outer conduit 128 when the cap 24 is fitted to the base 22, thereby forming a seal between the base 22 and the cap 24. A plurality of fluid outlets 168 extend through the surfaces 70, 72 of the divider 68 and provide fluid communication to and/or from the inner conduit passageway 144A at the upper first portion 158 of the storage cavity 36 and the fluid dispensing area 78 of the cap 24. The outer conduit 126 directs a flow of the fluid 28 in and/or out of the plurality of fluid outlets 168 and away from the outer conduit receiver 144B, thereby preventing the fluid 28 from exiting the base 22 through other areas between the cap 24 and the base 22. While the exemplary embodiment is illustrated with the plurality of fluid outlets 168 in the cap 24, it is foreseen that the cap 24 may be equipped with any number of fluid outlets, such as but not limited to a single fluid outlet, without deviating from the scope of the present invention.

The splashguard 66 and the lip 42 have substantially equal circumferences (although they are not illustrated to have the same shape). As such, when the cap 24 is fitted to the base 22, the splashguard 66 is aligned on the cap 24 with the lip 42 of the neck 48 of the base 22. In this manner, the neck 48 increases the structural integrity of the splashguard 66, which significantly decreases the likelihood of collapse of the splashguard 66, for instance, when the base 22 and the splashguard 66 are pressed against the facial contour 82 of the user.

The closure 26 is sized and shaped to securely mate with the perimeter sidewall 88 of the cap 24 and is, in the exemplary embodiment, of a generally circular shape. It is foreseen, however, that the closure 26 may be of any shape without deviating from the scope of the present invention. The closure 26 includes a top wall 174 with a circumferential cup-engagement skirt 176 depending therefrom. The top wall 174 and the cup-engagement skirt 176 cooperatively define a splashguard receiver 178. The splashguard receiver 178 is sized and shaped to substantially receive the splashguard 66 therein with the ocular-engagement edge 80 abutting an interior surface 180 of the top wall 174. The cup-engagement skirt 176 includes opposing inner and outer surfaces 182, 184 that are spaced from each other by inner and outer lower walls 185A, 185B with inner and outer lower edges 186A, 186B. The inner and outer lower walls 185A, 185B are spaced from each other and form a cup abutment receiver 187 with a cup abutment portion 188 therebetween. The cup abutment receiver 187 is operable to receive the upper edge 90 of the perimeter sidewall 88 of the cap 24, which abuts the cup abutment portion 188 of the closure 26. In this manner, a sealing engagement is provided when the closure 26 is fitted to the cap 24. Additionally, the inner lower wall 185A is operable to direct a flow of the fluid 28 away from the cup abutment receiver 187 and to the circumferential channel 98, thereby preventing the fluid 28 from exiting through other areas between the cap 24 and the closure 26.

A second locking element 190 extends axially from the inner surface 104 of the base-engagement skirt 102 and is defined by first and second cam surfaces 192, 194 that are oblique relative to the axial direction of extension of the second locking element 190. The first surface 192 extends from the lower edge 186 of the closure 26 to the second surface 194 and is angled at approximately 20° from a plane defined by the inner surface 182 of the cup-engagement skirt 176. The second surface 194 extends from the first surface 192 to the inner surface 182 of the cup-engagement skirt 176 and is angled at approximately 45° from the plane defined by the inner surface 182 of the cup-engagement skirt 176.

When the closure 22 is fitted to the cap 24, via a friction fit, snap-fit or the like, the first surface 192 of the second locking element 190 abuts the upper edge 90 of the perimeter sidewall 88. Due to the lesser angle of the first surface 192, that is, approximately 20°, the second locking element 190 slides over the upper edge 90, along the exterior surface 96 and past the lower edge 92. When removal of the closure of the cap 24 is attempted, the second surface 194 of the second locking element 190 abuts the lower edge 92 of the sidewall 88 and/or the spacer wall 86. Due to the greater angle of the second surface 194, that is, approximately 45°, the second locking element 190 is prevented from sliding past the lower edge 92 of the sidewall 88 and/or the spacer wall 86. In this manner, the second locking element 190 securely locks the closure 26 to the cap 24 after being fitted thereto.

A tamper indicator 202 is integrated into and severably secured to the cup-engagement skirt 176 at a top end 204 of the tamper indicator 202 and includes the second locking element 190. In this embodiment, the tamper indicator 202 includes a pull tab 206 depending from the top end 204 of the tamper indicator 202. The pull tab 206 presents opposing inner and outer grasping surfaces 208, 210. The top end 204 defines a horizontal line-of-weakness having a lesser thickness than adjacent areas of the cup-engagement skirt 176. The top end 204 is operable to be severed from the cup-engagement skirt 176 when the pull tab 206 is pulled away from the cup-engagement skirt 176, as illustrated by FIG. 6. When the top end 204 is severed from the cup-engagement skirt 176, the second locking element 190 is removed from the closure 26 and removal of the closure 26 from the cap 24 and access to the fluid 28 are permitted. Thus, removal of the closure 26 from the cap 24 is prevented if the top end 204 of the tamper indicator 202 is at least partially secured to the cup-engagement skirt 176 and removal of the closure 26 from the cap 24 is permitted if the top end 204 of the tamper indicator 202 is severed from the cup-engagement skirt 176.

Upon manufacture of the base 22, the cap 24, and the closure 26, the fluid 28 is added to the storage cavity 36 via the mouth 44 of the base 22. In the exemplary embodiment, the storage cavity 36 is sized and shaped to store 16 oz or 32 oz of the fluid 28. It is foreseen, however, that the storage cavity 36 may be any size and/or shape to store any amount of the fluid 28 without deviating from the scope of the present invention. The cap 24 is then fitted to the base 22 via threading the cap 24 onto the base 22 until the first locking element 116 lockingly engages the rib 50 of the base 22. The closure 26 is then fitted to the cap 24 via pressing the closure 26 onto the cap 24 until the second locking element 190 engages the lower edge 92 of the sidewall 88 and/or the spacer wall 86 of the cap 24. The container 20 is then sterilized, at which point the container 20 may be stored until use of the fluid 28 is desired. It is noted that sterilization may be effected using any suitable method, such as steam treatment or irradiation. Preferably, the assembled and filled container is irradiated using radiation levels which will provide the desired sterilization without degrading the structural integrity of the container. Most preferably, the assembled and filled container is exposed to gamma rays during the sterilization process. With the terminal sterilization process and the closure 26 securely and sealingly overlying the dispensing cap 24, the sterilized condition of the fluid and the cap 24 is assured throughout storage and until use. The tamper indicator 202 provides visual confirmation to the user that the sterilized condition of the assembled and filled container 20 has not been altered or adulterated.

Figure 7:
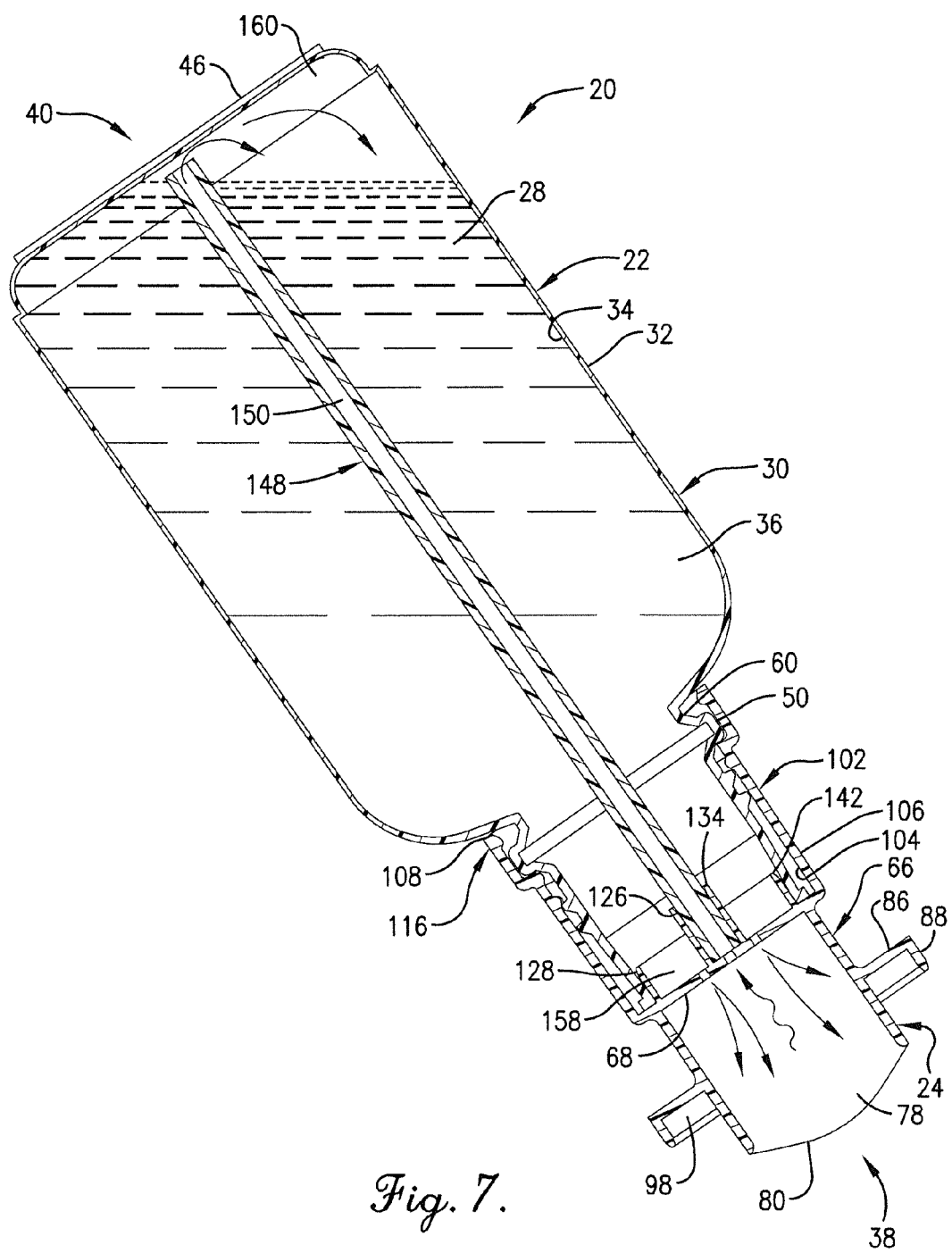
FIG. 7 is a cross-sectional view of the eyewash dispensing container illustrated in FIG. 1, illustrating the system inverted with fluid exiting outputs and entering an input.

To use the fluid 28, the pull-tab 206 of the tamper indicator 202 is pulled by grasping the opposing inner and outer grasping surfaces 208, 210 so that the top end 204 is severed from the cup-engagement skirt 176. The second locking element 190 is removed from the closure 26 with the removal of the tamper indicator 202, which permits removal of the closure 26 from the cap 24. The closure 26 is then removed and the fluid 28 is accessible. The base 22 is then inverted with the ocular engagement edge 80 pressed against the facial contour 82 of the user, as illustrated in FIG. 1. Gravity causes the fluid 28 to pass through the fluid outlets 168 at a sufficient rate to wash the eye 84 of the user. As the fluid 28 is exiting the storage cavity 36 via the fluid outlets 168, fluid, that is, air is received through the vent hole 156 and transported from the first portion 158 of the storage cavity 36 to the second portion 160 of the storage cavity 36, which causes the fluid 28 to exit through the fluid outlets 168 at a steady rate without requiring any air intake through the fluid outlets 168, that is, "glugging" or the like (see FIG. 7).

Although the container 20 is designed to be used only once, it is foreseen that the container 20 may be reused by refilling with the storage cavity 36 with the fluid 28 via the mouth 44 of the base 22, fitting another of the closure 26 to the cap 24 with the tamper indicator 202 unsevered from the cup-engagement skirt 176 via pressing the closure 26 onto the cap 24, and/or sterilizing the container 20 via gamma ray irradiation or the like.

Turning to FIGS. 8-11, another embodiment of the present invention, that is, an eyewash dispensing container is generally illustrated in use by the user. The system generally includes a container 320 having a base 322 and a fluid dispensing cap having a nozzle 324 and a container cover or closure 326. The nozzle 324 and the closure 326 are securely engaged with and fitted to the base 322 to securely store a fluid within the base 322. The closure 326 includes a tamper indicating, break-away cap 328 that is integrally formed therewith.

The base 322 includes a body 330 with opposing outer and inner surfaces 332, 334. The outer surface 332 of the base 322 presents a grasping surface for the user to handle the container 320. The outer and inner surfaces 334 of the base 322 cooperatively define a storage cavity 336 within the base 322 operable to store fluid. In the exemplary embodiment, the base 322 is of a generally cylindrical shape. It is foreseen, however, that the base 322 may be of any shape without deviating from the scope of the present invention.

Figure 9:
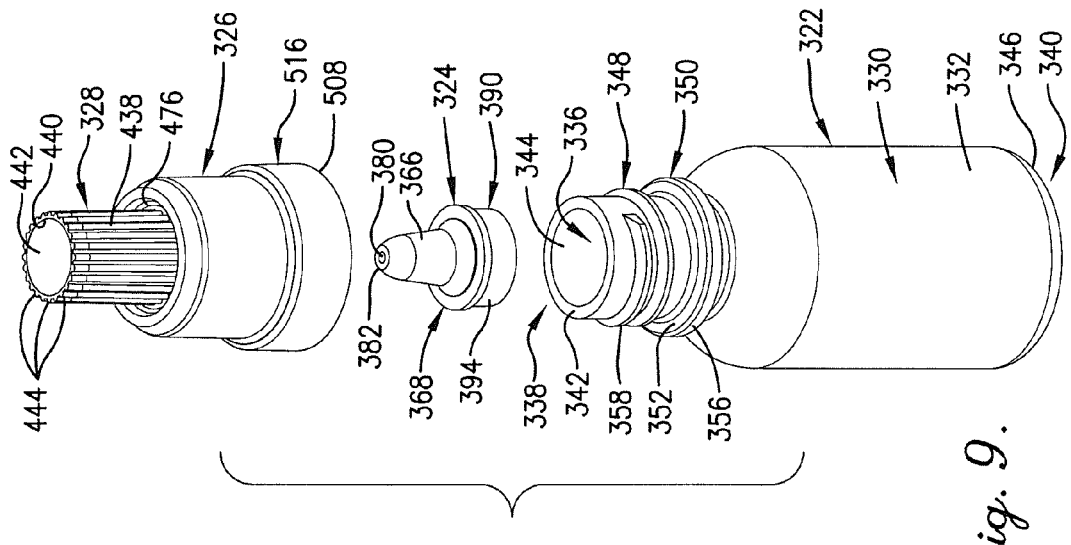
FIG. 9 is an exploded perspective view of the eyewash dispensing container illustrated in FIG. 8, illustrating a nozzle and a cup exploded from a container.
Figure 8:
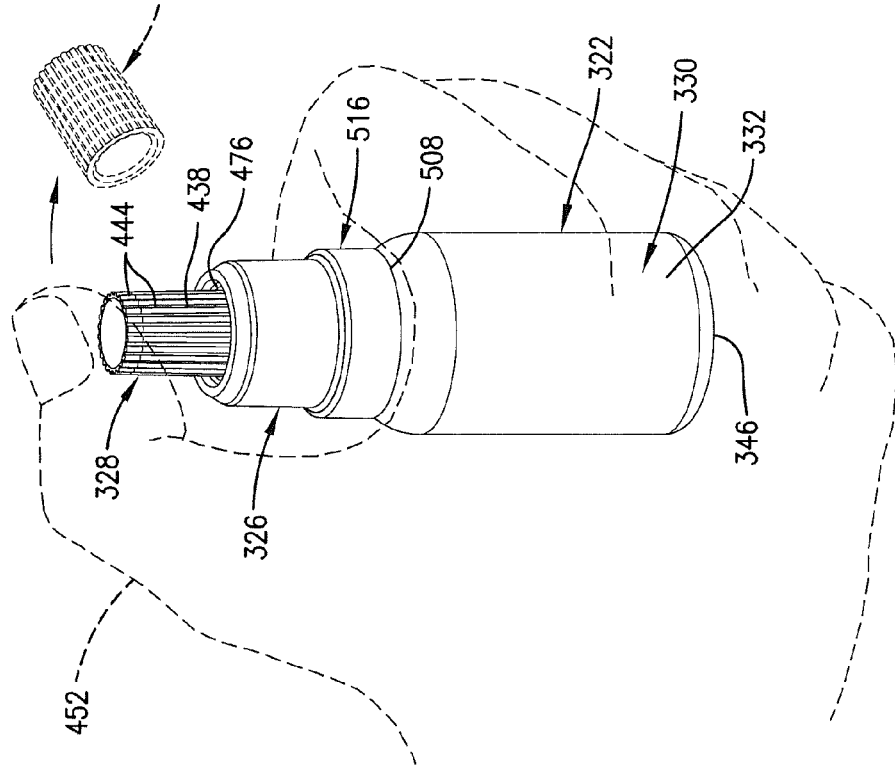
FIG. 8 is a perspective view of an eyewash dispensing container in accordance with another embodiment of the present invention illustrating a closure being removed by a user.

The storage cavity 336 is open at an open end 338 of the base 322 and closed at a closed end 340 of the base 322. The open end 338 includes a circumferential lip 342 that defines a mouth 344 through which fluid is received in and/or dispensed from the storage cavity 336. The closed end 340 of the base 322 includes an end wall 346 operable to support the container 320 in an upright configuration, as illustrated by FIG. 9.

The base 322 tapers when traveling from the closed end 340 to the open end 338 and ultimately presents a neck 348. The neck 348 includes a circumferential rib 350 that protrudes outwardly from the base 322 and is defined by opposing upper and lower horizontal surfaces 352, 354 that are spaced from each other by a vertical surface 356, which is a portion of the outer surface 332 of the base 322. Also protruding outwardly from the neck 348 of the base 322 is an external thread 358, which is oriented between the rib 350 and the open end 338 along the neck 348 of the base 322. On a side of the rib 350 opposite to the thread 358 is a receiver portion 360 of the neck 348. The receiver portion 360 has a smaller circumference than a circumference of the rib 350.

The nozzle 324 is sized and shaped to present a dropper outlet configured to dispense drops of eyewash fluid. Furthermore, the nozzle 324 securely mates with the neck 348 of the base 322 by extending partially through the mouth 344 of the base 322. The nozzle 324 is, in the exemplary embodiment, of a generally cylindrical shape. It is foreseen, however, that the nozzle 324 may be of any shape without deviating from the scope of the present invention. The nozzle 324 includes a conical wall 366 that extends upwardly from an abutment ridge 368 and defines a nozzle cavity 370 (see FIG. 11). The abutment ridge 368 has opposing upper and lower surfaces 372, 374.

A fluid inlet-outlet 380 extends through the conical wall 366 at a tip 382 thereof and permits fluid communication to and/or from the storage and nozzle cavities 336, 370 to an outside of the system for use by the user. While the exemplary embodiment is illustrated with the single fluid inlet-outlet 380 in the nozzle 324, it is foreseen that the nozzle 324 may be equipped with any number of fluid inlets or vent holes and/or fluid outlets, such as but not limited to two fluid inlet-outlets and/or one vent hole and one fluid outlet, without deviating from the scope of the present invention.

The nozzle 324 further includes an interior container-engagement skirt 390 that depends from the lower surface 374 of the abutment ridge 368. The interior container-engagement skirt 390 has opposing inner and outer surfaces 392, 394 that are spaced from each other by a lower edge 396. The interior container-engagement skirt 390 is sized and shaped to slidably engage the base 322 through the mouth 344 of the base 322 with the lip 342 of the base 322 abutting the lower surface 374 of the abutment ridge 368 of the nozzle 324. In this manner, a secure engagement between the nozzle 324 and the base 322 is formed when the nozzle 324 is fitted onto the neck 348 of the base 322 via a friction fit, snap fit, or the like.

The closure 326 is sized and shaped to securely mate with the neck 348 of the base 322 and is, in the exemplary embodiment, of a generally cylindrical shape. It is foreseen, however, that the closure 326 may be of any shape without deviating from the scope of the present invention. The closure 326 includes the break-away cap 328 integrally formed with and extending upwardly from a top wall 414 of the closure 326. The top wall 414 has opposing upper and lower surfaces 416, 418. The closure 326 includes an inner capping wall 432 and an outer ribbed wall 434 having a common base 436.

The inner capping wall 432 is sized and shaped to correspond to the shape of the conical wall 366. When the closure 326 is fitted to base 322 and the break-away cap 328 is secured to the closure 326, the inner capping wall 432 closes the fluid inlet-outlet 380 and forms a seal between the break-away cap 328 and the nozzle 324. The outer ribbed wall 434 includes opposing outer and inner surfaces 438, 440 that cooperatively define an interior void 442. The outer surface 438 includes a plurality of ribs 444. The base 436 is integrally formed with the top wall 414 at a line-of-weakness 450 to facilitate severing of the break-away cap 328 from the top wall 414 when a force is exerted on the outer ribbed wall 434, for instance, via a thumb 452 of the user. The plurality of ribs 444 increases friction between the break-away cap 328 and the thumb 452 of the user, for instance, during removal of the break-away cap 328 from the top wall 414. When the break-away cap 328 is broken away from the top wall 414, the fluid inlet-outlet 380 is exposed thereby permitting fluid stored in the storage cavity 336 to be dispensed from the container 320.

Spaced radially from the break-away cap 328 along the top wall 414 is a perimeter sidewall 468 that extends substantially parallel to the outer ribbed wall 434 of the break-away cap 328. The sidewall 468 includes opposing interior and exterior surfaces 470, 472 that are spaced from each other by an upper edge 474. The sidewall 468 and the outer ribbed wall 434 cooperatively define a circumferential channel 476 that extends around the break-away cap 328. Additionally, the sidewall 468 creates a buffer zone between the sidewall 468 and the line-of-weakness 450. In this manner, the sidewall 468 protects the line-of-weakness 450 from inadvertent breakage. While it is foreseen that the sidewall 468 may have any shape, in the exemplary embodiment, the sidewall 468 is of a substantially circular shape.

Figure 10:
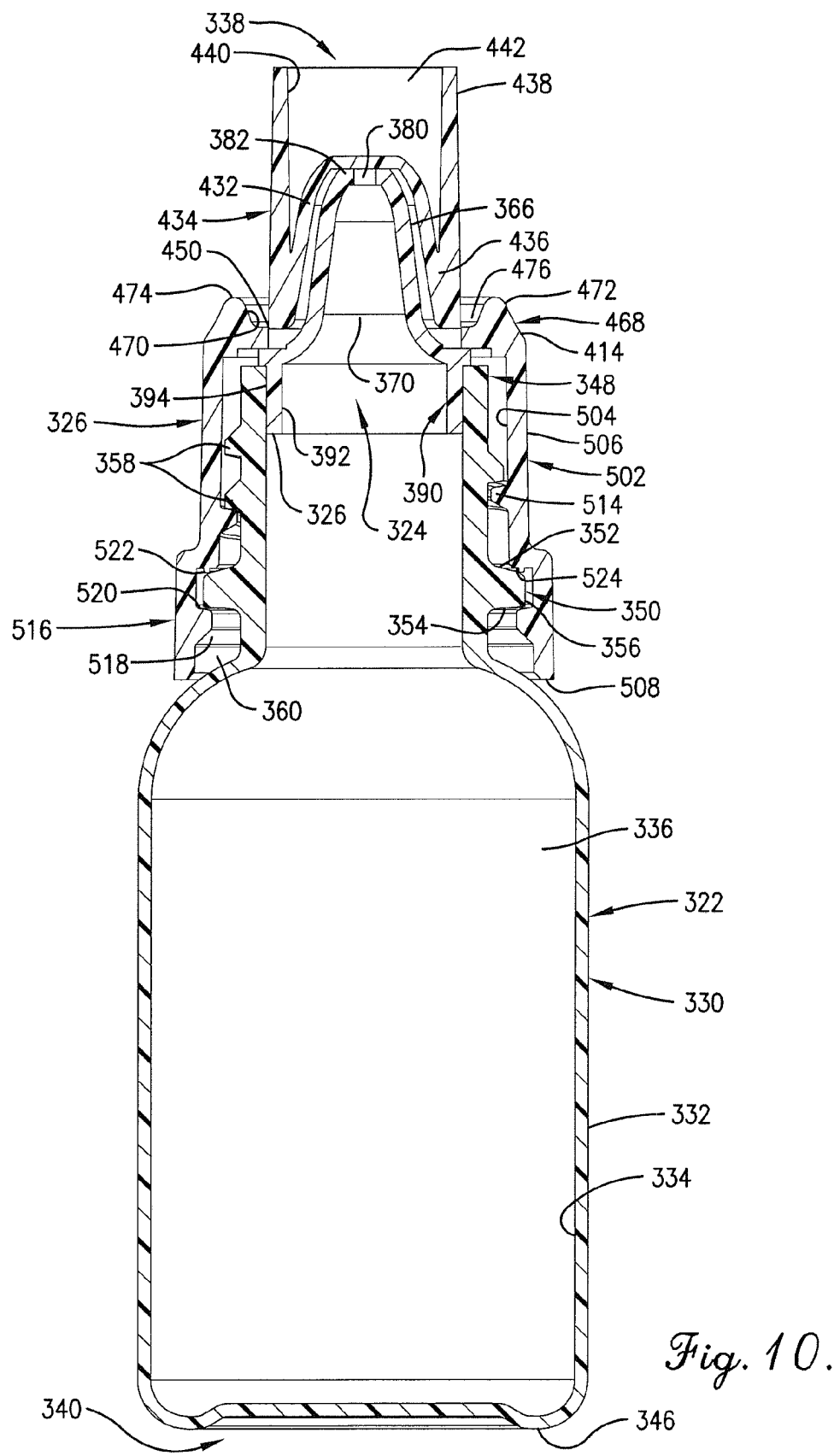
FIG. 10 is a cross-sectional view of the eyewash dispensing container illustrated in FIG. 8.

The closure 326 further includes a container-engagement skirt 502 that depends from the lower surface 418 of the top wall 414. The container-engagement skirt 502 has opposing inner and outer surfaces 504, 506. On an opposite end of the container-engagement skirt 502 relative to the top wall 414 is a container-abutment edge 508, as illustrated in FIG. 10. Protruding inwardly from the inner surface 504 of the container-engagement skirt 502 is an internal thread 514, which is sized and shaped to securely mate with the external thread 358 of the neck 348 of the base 322. In this manner, a secure engagement between the closure 326 and the base 322 is formed when the closure 326 is threaded onto the neck 348 of the base 322.

Also protruding inwardly or axially from the inner surface 504 of the container-engagement skirt 502 and between the internal thread 514 and the container-abutment edge 508 is a locking element 516. The locking element 516 is defined by first and second surfaces 518, 520 that are oblique relative to the axial direction of extension of the locking element 516. The first surface 518 extends from the container-abutment edge 508 to the second surface 520 and is angled at approximately 45° from a plane defined by the inner surface 504 of the container-engagement skirt 502. The second surface 520 extends from the first surface 518 to the inner surface 504 of the container-engagement skirt 502 and is angled at approximately 80° from the plane defined by the inner surface 504 of the container-engagement skirt 502.

When the closure 326 is fitted to the base 322, the first surface 518 of the locking element 516 abuts the upper horizontal surface 352 of the rib 350. Due to the lesser angle of the first surface 518, that is, approximately 45°, the locking element 516 slides over the rib 350 and is received by the receiver portion 360 of the neck 348. Additionally, a nozzle abutment surface 521 of the closure 326 abuts the upper surface 372 of the abutment ridge 368 of the nozzle 324. In this manner, the closure 326 clamps the nozzle 324 to the base 322. When removal of the closure 326 from the base 322 is attempted, the second surface 520 of the locking element 516 abuts the lower horizontal surface 354 of the rib 350. Due to the greater angle of the second surface 520, that is, approximately 80°, the locking element 516 is prevented from sliding over the rib 350. In this manner, the locking element 516 securely locks the closure 326 to the base 322 after being fitted thereto. A nub 522 depends from a portion 524 of the inner surface 504 of the container-engagement skirt 502 to securely abut the upper horizontal surface 352 of the rib 350 when the closure 326 is fitted to the base 322.

Upon manufacture of the base 322, the nozzle 324, and the closure 326, fluid is added to the storage cavity 336 via the mouth 344 of the base 322. In the exemplary embodiment, the storage cavity 36 336 sized and shaped to store between 0.5 oz to 8 oz of fluid. It is foreseen, however, that the storage cavity 336 may be any size and/or shape to store a variety of fluid amounts without deviating from the scope of the present invention. The nozzle 324 is then fitted to the base 322 via pressing the nozzle 324 to the base 22 until the lower surface 374 of the abutment ridge 368 of the nozzle 324 abuttingly engages the lip 342 of the base 322. The closure 326 is then fitted to the base 322 via threading the closure 326 to the base 322 until the locking element 516 engages the lower horizontal surface 354 of the rib 350 and the nozzle 324 is clamped to the base 322 via the closure 326. The container 320 is then radiated via gamma rays or the like to sterilize the container 320, at which point the container 320 may be stored until use of the fluid is desired.

To use the fluid, the break-away cap 328 is severed from the closure 326 by exerting a force or pressing against the outer ribbed wall 434 of the break-away cap 328, for instance, via the thumb 452 of the user. The plurality of ribs 444 creates friction between the break-away cap 328 and the thumb 452 of the user, which facilitates severing of the break-away cap 328 from the closure 326. With the break-away cap 328 broken away, the fluid inlet-outlet 380 is exposed and the fluid stored in the storage cavity 336 is accessible. The base 322 is then inverted with the nozzle 324 directed to a surface to be rinsed, e.g., the eye 84 of the user. The base 322 is then compressed, which causes the fluid to be dispensed via the fluid inlet-outlet 380 at a sufficient rate to wash the eye 84 of the user.

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. An eyewash dispensing container comprising:
   a base presenting a storage cavity in which eyewash fluid is contained,
   said base including a neck that defines an opening in communication with the storage cavity to permit fluid to be discharged from the base;
   a fluid dispensing cap sealingly secured to the base in a covering relationship with the opening,
   said dispensing cap including a fluid outlet through which fluid is discharged from the storage cavity,
   said dispensing cap including a cap skirt circumscribing the neck of the base, with the cap skirt and neck cooperatively presenting interlocking structure to restrict removal of the dispensing cap from the base; and
   a removable closure sealingly overlying the dispensing cap to prevent fluid dispensing until removed,
   said removable closure providing tamper indication once removed so as to facilitate only single use of the container,
   said dispensing cap further including a splashguard that presents an ocular-engagement edge shaped to conform to a facial contour,
   said splashguard and said neck being at least substantially aligned and in direct contact when the dispensing cap is secured to the base, with at least a portion of the ocular-engagement edge and the neck being aligned, such that the neck increases the structural integrity of the splashguard when the ocular-engagement edge is pressed against the facial contour.

2. The eyewash dispensing container as claimed in claim 1, said cap skirt and neck being threadably interconnected.

3. The eyewash dispensing container as claimed in claim 2,
   said interlocking structure including a locking element projecting inwardly from the cap skirt and a collar projecting outwardly from the neck,
   said locking element and collar presenting interengaging surfaces that face in opposite, at least substantially axial directions.

4. The eyewash dispensing container as claimed in claim 3,
   at least one of said locking element and collar defining a cam surface that is oblique relative to the axial directions to facilitate attachment of the dispensing cap on the base.

5. The eyewash dispensing container as claimed in claim 1,
   said dispensing cap comprising an eyewash cup at least in part defined by the splashguard.

6. The eyewash dispensing container as claimed in claim 1,
   said removable closure including a top wall and a skirting depending from the top wall, said skirting sealingly engaging the dispensing cap.

7. The eyewash dispensing container as claimed in claim 6,
   said dispensing cap presenting a substantially axially facing shoulder,
   said skirting including a inwardly extending circumferential locking rib that engages the shoulder once the removable closure is snapped onto the dispensing cap so as to restrict removal of the removable closure from the dispensing cap.

8. The eyewash dispensing container as claimed in claim 7,
   said removable closure including a tamper indicator that allows at least part of the skirting to be separated from the locking rib, with such separation permitting the removable closure to be removed from the dispensing cap.

9. The eyewash dispensing container as claimed in claim 8,
   said tamper indicator including a line of weakness projecting from and extending along the locking rib to define a pull tab, with said at least part of the skirting being the pull tab,
   at least part of said locking rib being located on the pull tab.

10. The eyewash dispensing container as claimed in claim 7,
    said dispensing cap comprising an eyewash cup at least in part defined by the splashguard,
    said dispensing cap including a perimeter sidewall connected to and spaced from the splashguard via a spacer, with the spacer defining the shoulder,
    said skirting extending alongside and in engagement with the perimeter sidewall.

11. The eyewash dispensing container as claimed in claim 10, said perimeter sidewall and spacer defining a circumferential channel therebetween, the circumferential channel having a variable width.

12. The eyewash dispensing container as claimed in claim 1,
said dispensing cap including a vent hole and a vent tube in communication with the vent hole,
said vent tube projecting inwardly into the base to facilitate venting of the storage cavity to ambient pressure when the container is inverted and eyewash fluid is dispensed.

13. The eyewash dispensing container as claimed in claim 12,
said base presenting a closed end opposite the neck,
said vent tube presenting a terminal end opposite the vent hole that is immediately adjacent the closed end of the base.

14. The eyewash dispensing container as claimed in claim 1, said neck including a lip that defines the opening,
said splashguard and said lip being at least substantially aligned and in direct contact when the dispensing cap is secured to the base, such that the lip increases the structural integrity of the splashguard when the splashguard is pressed against the facial contour.

15. The eyewash dispensing container as claimed in claim 14, said ocular-engagement edge and said lip having different shapes.

16. The eyewash dispensing container as claimed in claim 15, said ocular-engagement edge having an oval shape, said lip having a circular shape.

* * * * *